United States Patent [19]

Nagakura et al.

[11] 4,052,457

[45] Oct. 4, 1977

[54] 3,7,11,11-TETRAMETHYL-SPIRO-[5,5]UNDECA-8-ENE-1-ONE

[75] Inventors: Akira Nagakura, Kawaguchi; Michio Moroe, Musashino; Yasuto Koyama; Haruki Kurihara, both of Tokyo, all of Japan

[73] Assignee: Takasago Perfumery Co., Ltd., Tokyo, Japan

[21] Appl. No.: 636,858

[22] Filed: Dec. 2, 1975

[30] Foreign Application Priority Data

Dec. 2, 1974 Japan .................................. 49-138613
Dec. 2, 1974 Japan .................................. 49-138614

[51] Int. Cl.$^2$ ...................... C07C 45/00; C07C 49/48; C07C 49/54
[52] U.S. Cl. .......................... 260/586 G; 131/17 R; 260/586 C

[58] Field of Search ........................ 260/586 G, 586 C

[56] References Cited

U.S. PATENT DOCUMENTS

| 3,681,470 | 8/1972 | Kitchens et al. | 260/586 C |
| 3,754,037 | 8/1973 | Kitchens et al. | 260/586 C |
| 3,852,358 | 12/1974 | Hall et al. | 260/586 C |
| 3,894,088 | 7/1975 | Naegeli | 260/586 G |

*Primary Examiner*—Norman Morgenstern
*Attorney, Agent, or Firm*—Sughrue, Rothwell, Mion, Zinn and Macpeak

[57] ABSTRACT

A novel spiro compound, 3,7,11,11-tetramethylspiro[5,5]-undeca-8-ene-1-one for altering the flavor or aroma of tobacco products. The spiro compound is prepared by reacting pulegone and piperylene in a solvent in the presence of a Lewis acid catalyst.

5 Claims, No Drawings

3,7,11,11-TETRAMETHYL-SPIRO-[5,5]UNDECA-8-ENE-1-ONE AND A PROCESS FOR ITS PREPARATION

BACKGROUND OF THE INVENTION

1. Field of the Invention

The present invention relates to a novel spiro compound, to a process for producing the same and to its use for altering the flavor and aroma of tobacco products.

2. Description of the Prior Art

Tobacco products give various flavors and aromas when they are smoked, and the flavors and aromas are quite important factors in evaluating the quality of the tobacco products and satisfying the tastes of smokers. However, tobaccos contain various materials and impurities and these materials sometimes cause an undesirable burnt smell, a fishy smell, or an irritative taste during smoking. Therefore, various flavoring materials or compositions have been employed to impart flavors to such tobaccos to eliminate such undesirable smells and tastes during smoking.

SUMMARY OF THE INVENTION

The inventors have made various studies on altering the flavors and aromas of tobacco products and have investigated various spiro compounds for the aforesaid purpose, and, as a result thereof, the inventors have discovered that a novel spiro compound, 3,7,11,11-tetramethyl-spiro[5,5]undeca-8-ene-1-one, represented by the formula

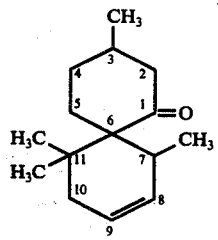

has excellent flavoring characteristics and can prevent or control the formation of the aforesaid undesirable smell of tobacco when incorporated therein, enhance desired flavors and aromas specific to leaf tobacco, and remarkably improve the flavors and aromas of tobacco products. It has further been found that the aforesaid novel spiro compound can be prepared readily from easily available raw materials.

One object of this invention is, therefore, to provide a novel spiro compound having excellent flavor characteristics.

Another object of this invention is to provide a novel spiro compound suitably used to altering the flavors and aromas of tobacco products.

Still another object of this invention is to provide a process of producing the aforesaid novel spiro compound.

Yet a further object of this invention is to provide a process for altering the flavors and aromas of tobacco products using the aforesaid spiro compounds.

The aforesaid objects of this invention can be attained by the spiro compound, 3,7,11,11-tetramethyl-spiro[5,5]undeca-8-ene-1-one, having the aforesaid formula.

According to this invention, there is provided a process of producing the aforesaid spiro compound which comprises reacting pulegone and piperylene in a solvent at a temperature of about 0° C to the reflux temperature, preferably room temperature (e.g., about 20°–30° C), at atmospheric pressure in the presence or absence of a Lewis acid catalyst.

According to this invention, there is further provided a process of altering the flavors and aromas of tobacco products which comprises adding thereto the aforesaid spiro compound during the preparation of the tobacco products as later explained.

These and other objects of this invention will become apparent from the following description.

DESCRIPTION OF THE PREFERRED EMBODIMENTS

As described above, the novel spiro compound of this invention, 3,7,11,11-tetramethyl-spiro[5,5]undeca-8-ene-1-one, shown by the formula below, is prepared by reacting pulegone and piperylene in a solvent in the presence or absence of a Lewis acid catalyst, the reaction of which is shown by the following reaction formula.

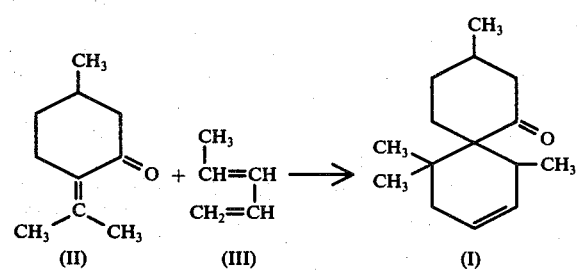

Pulegone (II) in the above reaction formula exists in natural essential oils such as in perilla oil and is commercially available as recovered from such essential oils.

On the other hand, piperylene (III) is also commercially available as the industrial raw material 1,3-pentadiene.

The spiro compound of formula I is generally produced by subjecting pulegone of formula II and piperylene of formula III to Diels-Alder reaction conditions and in this case, it is preferred to use 1–4 moles of piperylene per mole of pulegone. The reaction is carried out in a solvent inert to the Diels-Alder reaction which dissolves all starting materials.

In the Diels-Alder reaction of this invention, any organic solvent which does not correspond to compounds containing therein conjugated double bonds or dienophile compounds, both compounds being involved in the Diels-Alder reaction per se, can be used in this invention. Suitable examples of such organic solvents used are dichloromethane, carbon tetrachloride, chloroform, benzene, toluene, n-hexane, etc., in an amount of 5–20 times by volume that of the raw materials.

The reaction of this invention can be carried out in the presence of a Lewis acid catalyst.

Any Lewis acid (an electron-pair acceptor) can be used in this invention, in particular, aluminum chloride, titanium tetrachloride, stannic chloride, and ferric chloride are most preferred. By carrying out the reaction of pulegone and piperylene for 10–48 hours at room temperature to the refluxing temperature using 0.1–1 mole of the Lewis acid per mole of pulegone, the spiro compound of formula I is obtained at an average yield of higher than 85%. The reaction proceeds even when the catalyst is not used, but in this case reaction is conducted for 50-100 hours using the pressure and temperature conditions set out above.

The reaction mixture thus obtained is first washed with, for example, a 10% aqueous hydrochloric acid solution, to eliminate the catalyst used. In this case, washing only with water is not preferred since gellation occurs due to the formation of aluminum hydroxide, etc., which renders difficult the separation of the reaction mixture. The resultant product is then washed with, for example, a 5% aqueous hydrogen carbonate solution, to neutralize the hydrochloric acid, followed by washing with, for example, a saturated aqueous sodium chloride solution for neutralization and salting-out.

After recovering unreacted piperylene and the solvent by distillation at from atmospheric pressure to about 100 mmHg, the reaction product is distilled under reduced pressure, e.g., about 100 mmHg or less, to obtain the spiro compound of formula I. In the reaction of this invention almost all the pulegone reacts. In particular, when equimolar or more piperylene is used, the reaction ratio is increased and the presence of unreacted material can be reduced.

The spiro compound of formula I thus obtained is an oily material possessing a wood-like flavor. The spiro compound thus obtained is also quite useful as a flavoring material capable of remarkably improving the flavor and aroma of tobacco products.

To alter the flavor and aroma of tobacco products, the spiro compound of this invention is added to the tobacco products, and in this case the spiro compound may be added to the tobacco products in any stage of producing them and by any means. For example, it is advantageous to spray the spiro compound onto tobacco, before or after cutting as a solution or emulsion in a suitable solvent such as ethanol, propylene glycol, water, etc. Furthermore, the flavor and aroma of stem or sheet tobacco, substitutes for tobacco mainly composed of cellulose, pipe tobacco, cigars, cigarette tobacco, etc., can also be improved by adding thereto the spiro compound of this invention in any stage of producing these products. Still further, the aforesaid flavor improving effect can be also obtained by adding the spiro compound to cigarette paper and paper used in cigar manufacture, pastes for cigarettes, cigarette or pipe filters, in short, tobacco products in general, etc.

The spiro compound of this invention will generally be sprayed onto tobacco as a 0.1 to 1.0% solution or emulsion for ease of application. When used as an emulsion, an appropriate amount of an emulsion stabilizer such as dextrin or the like can be combined therewith for use, if desired.

The amount of the spiro compound added to the tobacco product depends upon the kind, quality, use, etc., of the tobacco product, but is most preferably about 0.001-0.05% by weight of the spiro compound based on the weight of the tobacco present (dry weight at normal room conditions). Application to the tobacco leaves themselves is most preferred.

The invention will now be illustrated by several examples, but it will be understood that these examples are illustrative only and the invention is not restricted to these examples.

EXAMPLE 1

In a 500 milliliter reaction flask equipped with a reflux condenser, a thermometer, a dropping funnel, and a stirrer were placed 31 g (0.2 mole) of pulegone, 240 ml. of benzene, and 6.7 g (0.05 mole) of fine powders of commercially available aluminum chloride followed by stirring to dissolve the components in benzene. Then, while maintaining the solution at 10° C with ice-cooling, 50 ml. (0.5 mole) of piperylene was dropwise added to the solution over a period of 1 hour. Thereafter, the resultant mixture was stirred for 48 hours at room temperature to complete the reaction. The reaction mixture was washed twice with 100 ml. of an aqueous 10% hydrochloric acid solution, subsequently washed with 100 ml. of an aqueous 5% sodium hydrogen carbonate solution and twice with 100 ml of a saturated aqueous sodium chloride solution, and after drying the reaction mixture with anhydrous sodium sulfate, unreacted piperylene and benzene were recovered by distillation at atmospheric pressure. Then, by subjecting the residue to vacuum distillation at a pressure of 2-3 mmHg, 41 g (yield 93%) of the desired spiro compound of formula (I) having a boiling point of 118°-125° C/2-3 mmHg was obtained as an oily fraction. Except for the distillation, all reactions were at atmospheric pressure. The results of an analysis of the product were as follows:

$n_D^{20}$: 1.5020, $d_{20}^{20}$: 0.9808.

MS spectra: $M^+$ (molecular ion) 220, $M^+ - CH_3$ 205, and $M^+ - CH_3 - CO$ 177.

IR spectra:
 1689 cm.$^{-1}$ (spiro ring α-position ketone characteristic adsorption),
 698 cm.$^{-1}$ (cis 2-substituted olefin characteristic adsorption), and
 710 cm.$^{-1}$ (cis 2-substituted olefin characteristic absorption).

NMR spectra:

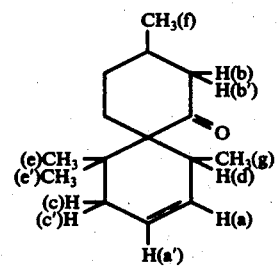

H(a), H(a'): 5-6 ppm., multiplet, 2H,
H(b), H(b'), H(c), H(c'), H(d), methylene (4H), methine (1H): near 1.2 ppm. -3.2 ppm., multiplet, 10 H, and
H(e), H(e'), H(f), H(g): methyl, singlet, singlet, doublet, doublet; total 12H: near 0.8-1.15 ppm.

EXAMPLE 2

The procedure of Example 1 was followed except for using titanium tetrachloride instead of aluminum chloride. The same results as in Example 1 were obtained.

EXAMPLE 3

The procedure of Example 1 was followed except for using stannic chloride instead of aluminum chloride. The same results as in Example 1 were obtained.

EXAMPLE 4

By following the same procedure as in Example 1 for 96 hours without using the aluminum chloride powder, the desired compound was obtained in a yield of 80%.

EXAMPLE 5

Onto 20 g of a cut tobacco (ca. 0.5-1 mm in diameter) prepared by loosening the tobacco from a commercially available cigarette "Wakaba" without the paper (selected as a low-grade tobacco product by nine expert panels) there was uniformly sprayed 1 g. of an ethanol solution of 0.1 wt. % of the spiro compound of this invention. After evaporating off the ethanol, 20 cigarettes were prepared using the cut tobacco thus treated by means of a manual cigarette-making device, and the flavor of the cigarettes was compared with that of an otherwise identical non-treated cigarettes by nine panels. The nine panels concluded that the irritative smell and taste of the original cigarettes were remarkably reduced by the addition of the spiro compound, i.e., the spiro compound had the remarkable effect of controlling the undesirable irritative smell and taste of the cigarettes.

EXAMPLE 6

The spiro compound of this invention was added to the tobacco from the commercially available cigarette "Cherry" (selected by nine expert panels as a middle-grade product having better flavor and aroma than "Wakaba") and cigarettes formed therefrom in the same manner as in Example 5; comparison to unreacted "Cherry" cigarettes was carried out as in Example 5. The nine panels concluded that the flavor and aroma of the cigarettes thus treated with the spiro compound of formula (I) became quite mild, and the "Cherry" cigarettes of middle grade which were treated with the spiro compound of formula (I) illustrated the flavor of a high-grade cigarette due to the addition of the wood-like flavor of the spiro compound.

While the invention has been described in detail and with reference to specific embodiments thereof, it will be apparent to one skilled in the art that various changes and modifications can be made therein without departing from the spirit and scope thereof.

What is claimed is:
1. 3,7,11,11-tetramethyl-spiro[5,5]undeca-8-ene-1-one.
2. A process of producing 3,7,11,11-tetramethyl-spiro-[5,5]undeca-8-ene-1-one which comprises reacting pulegone and piperylene in an inert solvent under Diels-Alder reaction conditions in the presence of a Lewis-acid catalyst.
3. The process of claim 2 wherein the amount of pulegone is 1-4 moles per mole of piperylene.
4. The process of claim 2 wherein said solvent is selected from the group consisting of dichloromethane, carbon tetrachloride, chloroform, benzene, toluene, or n-hexane.
5. The process of claim 2 wherein the reaction is carried out for 10-48 hours at room temperature to the refluxing temperature of the system in the presence of a Lewis acid catalyst.

* * * * *